United States Patent [19]

Randolph

[11] Patent Number: 5,347,066
[45] Date of Patent: Sep. 13, 1994

[54] ALKYLATION PROCESS FOR REACTING AN OLEFIN FEED BEING SUBSTANTIALLY FREE OF ISOBUTYLENE WHICH UTILIZES A HYDROGEN FLUORIDE AND SULFONE CATALYST

[75] Inventor: Bruce B. Randolph, Bartlesville, Okla.

[73] Assignee: Phillips Petroleum Company, Bartlesville, Okla.

[21] Appl. No.: 57,372

[22] Filed: May 6, 1993

[51] Int. Cl.$^5$ ............................................. C07C 2/62
[52] U.S. Cl. .................................. 585/724; 585/717; 585/730
[58] Field of Search ..................... 585/717, 724, 730

[56] References Cited

U.S. PATENT DOCUMENTS

| | | | |
|---|---|---|---|
| 3,795,712 | 3/1974 | Torck et al. | 260/671 C |
| 3,810,955 | 5/1974 | Sobel | 260/683.49 |
| 3,998,903 | 12/1976 | Sobel | 260/683.48 |
| 4,058,575 | 11/1977 | Cahn et al. | 585/724 |
| 4,118,433 | 10/1978 | Innes | 260/683.51 |
| 4,262,155 | 4/1981 | Hutson, Jr. et al. | 585/717 |
| 4,581,474 | 4/1986 | Hutson, Jr. et al. | 568/697 |

*Primary Examiner*—Asok Pal
*Attorney, Agent, or Firm*—Charles W. Stewart

[57] ABSTRACT

A process for producing an alkylate product having an improved octane value from an olefin stream having a reduced concentration of the butene isomer of isobutylene. The olefin feed stream to the process system is substantially free of isobutylene and can have undergone prior processing to remove isobutylene therefrom. The olefin feed is subjected to an alkylation reaction catalyzed by a mixture of hydrogen fluoride and sulfone.

12 Claims, No Drawings

:::page-number
5,347,066
:::

ALKYLATION PROCESS FOR REACTING AN OLEFIN FEED BEING SUBSTANTIALLY FREE OF ISOBUTYLENE WHICH UTILIZES A HYDROGEN FLUORIDE AND SULFONE CATALYST

BACKGROUND OF THE INVENTION

The present invention relates to a hydrocarbon conversion process. Particularly, the present invention relates to a method of improving the quality of an alkylate product from the catalyzed alkylation of olefin hydrocarbons.

The recent trend toward the production of oxygenates for gasoline blending can result in the removal of significant quantities of the butene isomer isobutylene from feedstocks to existing commercial alkylation processes. This is because isobutylene is a feedstock to certain etherification processes that produce the oxygenate compound of methyl tertiary butyl ether (MTBE). While MTBE is a gasoline blending component that has a relatively high octane blending value, there can be a partially offsetting octane debit to a gasoline pool that results from the removal of isobutylene alkylate produced from the hydrogen fluoride catalyzed alkylation of isobutylene, since isobutylene alkylate itself has a reasonably high octane blending value that is in the range of from about 92.5 to about 93.5. When the isomer of isobutylene is removed from a hydrogen fluoride alkylation process feed, the quality of the resultant alkylate will generally be diminished due to the presence of alkylate produced from the alkylation of 1-butene which has a lower octane blending value than that of isobutylene alkylate. The octane blending value of 1-butene alkylate can range from about 89 to about 90.

SUMMARY OF THE INVENTION

Thus, it is an object of this invention to provide a process for producing a high octane alkylate product.

A further object of this invention is to provide an improved process for the alkylation of the butene isomer of 1-butene so as to provide an alkylate of 1-butene that has an improved octane value over that of 1-butene alkylate produced from conventional alkylation processes.

A still further object of this invention is to provide a new process for alkylating an olefin stream having removed therefrom the butene isomer of isobutylene to give an alkylate product having an enhanced octane value which is above that provided by certain conventional alkylation processes.

Accordingly, the process of the present invention can comprise the step of contacting an admixture of an isoparaffin and an olefin feed with an alkylation catalyst to produce an alkylate product. The olefin feed will generally have a low concentration of isobutylene thus making the olefin feed substantially free of isobutylene, and the alkylation catalyst can comprise hydrogen fluoride and a sulfone compound.

Another embodiment of the inventive process can include the step of separating a mixed olefin stream into an isobutene stream and an olefin feed wherein the isobutene stream comprises isobutene and the olefin feed having a substantial absence of isobutene and comprising 1-butene. The olefin feed is mixed with an isoparaffin to form an admixture followed by contacting the admixture with an alkylation catalyst that comprises hydrogen fluoride and sulfolane within a reaction zone to produce an alkylate product.

A further embodiment of the invention includes a method of improving the quality of an alkylate product produced from the alkylation of 1-butene in an alkylation process which uses a hydrogen fluoride-containing catalyst. To produce the improved alkylate product, the hydrogen fluoride-containing catalyst is provided with a concentration of a sulfone. An admixture of an isoparaffin and an olefin feed having a substantial absence of isobutylene but comprising 1-butene is contacted with the hydrogen fluoride-containing catalyst within a reaction zone to thereby produce the alkylate product.

A final embodiment of the inventive process is an improved alkylation process of the type including contacting, within a reaction zone, a mixed olefin stream, comprising 1-butene and isobutylene, and an isoparaffin with a hydrogen fluoride catalyst and producing an alkylate product. The improvement includes the step of removing from the mixed olefin stream, prior to contacting it with the hydrogen fluoride catalyst, a portion of the isobutylene contained therein to provide the mixed olefin stream having a reduced concentration of isobutylene. Additionally, the hydrogen fluoride catalyst is provided with a concentration of sulfone. These steps, in combination, provide for an enhanced quality of 1-butene alkylate produced from the hydrogen fluoride catalyzed alkylation of 1-butene.

DETAILED DESCRIPTION OF THE INVENTION

Certain of the processes described herein utilize as a feedstock an olefin feed that has a low concentration of the butene isomer of isobutylene, but preferably, the olefin feed is substantially free of isobutylene or has a substantial absence of isobutylene but comprising 1-butene. The olefin feed can further comprise other olefin compounds selected from the group consisting of propylene, 2-butene, pentene, hexene, and mixtures of two or more thereof. The olefin feed can be derived from any source which suitably provides an olefin feed comprising alkylable olefin compounds but which has a low concentration of isobutylene. The preferred feedstocks for the process of this invention can be derived from various refinery process streams particularly those mixed olefin streams produced from the catalytic cracking of petroleum hydrocarbons comprising predominantly hydrocarbons having from three ($C_3$) to five ($C_5$) carbon atoms.

The isoparaffin charge stock utilized in the process of the present invention suitably has from four to five carbon atoms per molecule. The term "isoparaffin" is used to mean a saturated aliphated hydrocarbon having a methyl group on the next-to-terminal carbon atoms, i.e., the beta carbon atoms and no other branches. Thus, the isoparaffin can suitably be isobutane or isopentane or mixtures of the two. Isobutane is the preferred isoparaffin. Other paraffinic hydrocarbons boiling in about the same temperature range can also be present in the charge stock of the inventive process. Normal paraffins such as propane, n-butane and n-pentane are essentially inert.

One aspect of the instant invention is the recognition that the removal of isobutylene from a typical mixed olefin feedstream to a conventional hydrogen fluoride catalyzed alkylation process can have the ultimate effect of removing from the alkylate product the high octane isobutylene alkylate. One purpose for removing isobutylene from the mixed olefin feedstream is to recover isobutylene for use as a feedstock to an etherification process for the production of methyl tertiary butyl ether (MTBE). Therefore, one element of the instant invention can include the removal of a portion, preferably a significant portion, of the isobutylene contained in a mixed olefin stream that can include such refinery streams as a $C_3$ to $C_5$ stream derived from the catalytic cracking of petroleum hydrocarbons to give an olefin feed having a reduced concentration of isobutylene below that of the mixed olefin stream. Generally, the refinery mixed olefin stream will comprise predominantly hydrocarbons having from three to five carbon atoms and will include a concentration of butylene olefins in the range of from about 5 to about 40 volume percent with the volumetric ratio of isobutylene to 1-butene being in the range of from about 1:3 (0.33) to about 3:1 (3). In the situation where a portion of the isobutylene is removed from the mixed olefin stream for use as a feedstock to an MTBE process, or for other purposes, generally, at least about 90 volume percent of the isobutylene contained in the mixed olefin stream is removed therefrom; but, preferably, at least 95 volume percent of the isobutylene contained in the mixed olefin stream can be removed therefrom to ultimately provide the olefin feed having a reduced concentration of isobutylene below that of the mixed olefin stream or an olefin feed that is substantially free of isobutylene. Thus, the olefin feed that is substantially free of isobutylene will generally have a volumetric ratio of isobutylene to 1-butene of less than about 1:3 (0.33), preferably, less than 1:5 (0.20) and, most preferably, less than 1:10 (0.1). The olefin feed can also be a mixture of predominantly $C_4$ olefin compounds having a substantial absence of isobutylene but comprising 1-butene. Thus, the isobutylene concentration of the olefin feed will generally be less than about 3 volume percent of the olefin feed, preferably, less than about 2 volume percent and, most preferably, the concentration is less than 1 volume percent of the olefin feed.

In one embodiment of the inventive process, an admixture of an isoparaffin and an olefin feed, both as earlier described herein, are contacted preferably within a reaction zone with an alkylation catalyst. It is a critical aspect of the inventive processes described herein for the alkylation catalyst to include a sulfone component; since, it is the combination of the use of an alkylation catalyst containing a sulfone and an olefin feed that is substantially free of isobutylene but which contains 1-butene that gives an alkylate of 1-butene having a higher octane than such an alkylate produced by using an alkylation catalyst consisting solely of hydrogen fluoride and, optionally, inert components. Thus, the alkylation catalyst of the inventive process can comprise, consist of, or consist essentially of hydrogen fluoride and a sulfone where the sulfone utilized in the alkylation catalyst will be present in an amount such that the weight ratio of hydrogen fluoride to the sulfone is in the range of from about 1:1 to about 40:1. A weight ratio of hydrogen fluoride to sulfone in the alkylation catalyst of less than 1:1 can have such a significantly negative impact upon alkylate quality when the composition is utilized as an alkylation reaction catalyst that the composition can become commercially ineffective as a catalyst. Thus, a 1:1 weight ratio of hydrogen fluoride to sulfone in the alkylation catalyst mixture is an important lower limit for this ratio. The alkylation catalyst composition that works best in the alkylation process will have a weight ratio of hydrogen fluoride to sulfone in the range of from about 1:1 to about 40:1. To achieve optimal benefits from the alkylation catalyst composition, the preferred catalyst mixture should have a weight ratio of hydrogen fluoride to sulfone in the range of from about 2.3:1 to about 19:1 and, more preferably, the weight ratio shall range from 3:1 to 9:1.

The sulfones suitable for use in this invention are the sulfones of the general formula

wherein R and R' are monovalent hydrocarbon alkyl or aryl substituents, each containing from 1 to 8 carbon atoms. Examples of such substituents include dimethylsulfone, di n-propylsulfone, diphenylsulfone, ethylmethylsulfone, and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. The most preferred sulfone is sulfolane. These sulfones may also have substituents, particularly one or more halogen atoms, such as for example, chloromethylethylsulfone. These sulfones may advantageously be used in the form of mixtures.

It is preferred for the hydrogen fluoride component of the alkylation catalyst composition to be in anhydrous form, but, generally, the hydrogen fluoride component utilized can have a small amount of water. The amount of water present in the hydrogen fluoride and sulfolane mixture in no event can be more than about 30 weight percent of the total weight of the hydrogen fluoride component, which includes the water, and preferably, the amount of water present in the hydrogen fluoride component is less than about 10 weight percent. Most preferably, the amount of water present in the hydrogen fluoride component is less than 5 weight percent. When referring herein to the hydrogen fluoride component of the alkylation catalyst composition of the invention, it should be understood that this term means either the hydrogen fluoride component as an anhydrous mixture or as a mixture that includes water. The references herein to weight percent water contained in the hydrogen fluoride component means the ratio of the weight of water to the sum weight of the water and hydrogen fluoride multiplied by a factor of 100 to place the weight ratio in terms of percent.

Through the combination of reducing the concentration of isobutene in the olefin feed and the use of an alkylation catalyst containing both hydrogen fluoride and a sulfone, the alkylate quality is improved or enhanced, particularly, the quality of 1-butene alkylate is improved. The improved alkylate will generally have a trimethylpentane (TMP) to dimethylhexane (DMH) ratio of at least about 3.5. Because the alkylate quality is improved as the TMP to DMH ratio increases, it is preferable for the alkylate to have the largest practical TMP to DMH ratio. However, because the practical upper limit for the TMP to DMH ratio is about 8.5, the expected range for this ratio is from about 3.5 to about 8.5. A preferred range for the TMP to DMH ratio is from about 4.0 to about 8.0. Most preferably, the range for the ratio of TMP to DMH is from 4.5 to 7.5.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The following examples demonstrate the advantages of the present invention. These examples are by way of illustration only, and are not intended as limitations upon the invention as set out in the appended claims.

EXAMPLE I

A continuous alkylation reactor system was employed for the experiments of which the results are summmarized in Example II. A tubular reactor having the dimensions of 2′ length × 1″ diameter was fitted with a feed introduction nozzle and acid recirculation lines. Feeds were pumped into the reactor through the nozzle with a 0.01″ orifice. The reactor effluent was directed to a sight guage to effect separation of the acid and hydrocarbon product layers. The bottom acid layer was drawn out to a gear pump and returned to the reactor. The top hydrocarbon layer was directed through an alumina scrub system and collected in a product receiver. The reactor contents were held at approximately 90° F. throughout each experimental run.

Samples were taken at specified time intervals through a sampling port connected to the settler effluent line. The total product samples were then analyzed by gas chromatography. A mass selective detector was employed when peak identity confirmation was required.

Samples were also collected from the product receiver and analyzed by gas chromatography at specified intervals. These samples were then allowed to stand at room temperature to allow excess isobutane and other volatiles to evaporate. These samples were than combined and subjected to standard motor knock tests. These data are given in Table I.

EXAMPLE II

Table I shows the results for the alkylates obtained through the method described in Example I. These data show very similar product distributions for isobutene and 1-butene feeds when a 60/40 by weight HF/sulfolane mixture is used as catalyst. It is notable that the alkylate compositions are similar. This indicates the probable isomerization of 1-butene to isobutene prior to alkylation.

The TMP/DMH ratios are presented indicating the quality of the alkylate. In general, the higher the ratio of trimethylpentanes to dimethylhexanes, the higher the octane rating. As shown by the data presented in Table I, the TMP/DMH ratios of the alkylates produced by the alkylation of the isobutene and 1-butene feeds are similar in magnitudes. The TMP selectivity, defined as the fraction of $C_8$ material which is trimethylpentanes and expressed as percent, values are similar in magnitude for the isobutane and 1-butene feeds.

Also included for comparative purposes are data obtained from the HF catalyzed alkylation of isobutene and 1-butene feeds. These data were obtained in a pilot plant under very similar conditions to the present study (Temp. ≈80° F., I/O approximately 10). These data show superior performance for isobutene feed relative to 1-butene feed. The principal difference between these two alkylates is an increased production of dimethylhexanes at the expense of trimethylpentanes. The production of dimethylhexanes is believed to arise via reactions of 1-butene, such as dimerization and/or co-dimerizaton with isobutene, followed by some dimethylhexane isomerization. It is believed that the data are indicative of a lower level of 1-butene isomerization prior to alkylation.

The data presented in Table I show that the removal of isobutene from an olefin alkylation reactor feed in combination with the use of a mixture of hydrogen fluoride and sulfolane as an alkylation catalyst has the effect of improving or enhancing the quality of the alkylate produced by the alkylation of 1-butene olefin. As is shown, the 1-butene alkylate produced by an HF catalyzed alkylation reaction is significantly lower than the 1-butene alkylate produced by HF and sulfolane catalyzed alkylation reaction.

TABLE I

Comparative Data for the Alkylate of Isobutene and 1-Butene When a 60/40 (Weight/Weight) HF Sulfolane Catalyst is Used vs. HF Catalyst

|  | 60/40 HF/Sulfolane | | HF Catalyst | |
| --- | --- | --- | --- | --- |
|  | Isobutene Feed | 1-butene Feed | Isobutene Feed | 1-butene Feed |
| Feed I/O | 11.9 | 10.2 | ~10 | ~10 |
| Temp., °F. | 90 | 90 | ~80 | ~80 |
| Residence Time, Min. | 15 | 15 | ~60 | ~60 |
| Alkylate Composition (wt. %) | | | | |
| $C_5$-$C_7$ | 6.14 | 7.08 | 12.42 | 7.13 |
| $C_8$ | 77.55 | 79.90 | 80.02 | 85.59 |
| $C_9$+ | 16.11 | 12.57 | 7.56 | 7.28 |
| TMP | 66.43 | 68.81 | 71.21 | 65.63 |
| DMH | 10.92 | 10.91 | 8.81 | 19.77 |
| TMP/DMH | 6.08 | 6.31 | 8.08 | 3.32 |
| TMP Selectivity | 85.66 | 86.12 | 88.99 | 76.68 |

TABLE I-continued

Comparative Data for the Alkylate of Isobutene and 1-Butene When a 60/40 (Weight/Weight) HF Sulfolane Catalyst is Used vs. HF Catalyst

|  | 60/40 HF/Sulfolane | | HF Catalyst | |
| --- | --- | --- | --- | --- |
|  | Isobutene Feed | 1-butene Feed | Isobutene Feed | 1-butene Feed |
| (% of $C_8$) | | | | |

While this invention has been described in terms of the presently preferred embodiment, reasonable variations and modifications are possible by those skilled in the art. Such variations and modifications are within the scope of the described invention and the appended claims.

That which is claimed is:

1. A method of improving the quality of an alkylate product produced form the alkylation of 1-butene in an alkylation process which uses a hydrogen fluoride-containing catalyst, the method comprises the steps of:
   providing with said hydrogen fluoride-containing catalyst a concentration of a sulfone;
   contacting an admixture comprising an isoparaffin and an olefin feed having a volumetric ratio of isobutylene to 1-butene of less than 1:10, with said hydrogen fluoride-containing catalyst within a reaction zone; and
   producing said alkylate product.

2. A method as recited in claim 1 wherein said olefin feed has an absence of isobutylene.

3. A method as recited in claim 2 wherein said concentration of said sulfone in said hydrogen fluoride-containing catalyst is such as to give a weight ratio of hydrogen fluoride to sulfone in said hydrogen-fluoride containing catalyst in the range of from about 1:1 to 40:1.

4. A method as recited in claim 3 wherein said sulfone is sulfolane.

5. A method as recited in claim 4 wherein the contacting step occurs under alkylation conditions in which the alkylation reaction temperature is in the range of from about 0° F. to about 150° F. and the alkylation reaction pressure is sufficient to maintain said admixture of said isoparaffin and said olefin feed in the liquid phase.

6. A method as recited in claim 5 wherein the molar ratio of isoparaffin to olefin in said admixture is in the range of from about 2:1 to about 25:1.

7. An improved alkylation process of the type including contacting, within a reaction zone, a mixed olefin stream, comprising 1-butene and isobutylene, and an isoparaffin with a hydrogen fluoride catalyst and producing an alkylate product, wherein the improvement comprises:
   removing from said mixed olefin stream, prior to contacting it with said hydrogen fluoride catalyst, a portion of the isobutylene contained therein to provide an olefin feed having a volumetric ratio of isobutylene to 1-butene of less than 1:10; and
   providing a concentration of a sulfone in said hydrogen fluoride catalyst to thereby enhance the quality of 1-butene alkylate produced from the hydrogen fluoride catalyzed alkylation of 1-butene.

8. A process as recited in claim 7 wherein said mixed olefin stream includes a concentration of butylene olefins in the range of from about 5 to about 40 volume percent.

9. A process as recited in claim 8 wherein said olefin feed has an absence of isobutylene.

10. A process as recited in claim 9 wherein said concentration of said sulfone in said hydrogen fluoride catalyst provided is such as to give a weight ratio of hydrogen fluoride to sulfone in said hydrogen fluoride catalyst in the range of from about 1:1 to about 40:1.

11. A process as recited in claim 10 wherein the molar ratio of isoparaffin to olefin contacted within said reaction zone is in the range of from about 2:1 to about 25:1.

12. A process as recited in claim 11 wherein the contacting step occurs under alkylation conditions in which the alkylation reaction temperature is in the range of from about 0° F. to about 150° F. and the alkylation reaction pressure is sufficient to maintain said admixture of said isoparaffin and said olefin feed in the liquid phase.

* * * * *